(12) United States Patent
Kallenbach et al.

(10) Patent No.: US 12,070,592 B2
(45) Date of Patent: Aug. 27, 2024

(54) PUMP HAVING A ROTOR SENSOR FOR DETECTING PHYSIOLOGICAL PARAMETERS, FLOW PARAMETERS, AND MOVEMENT PARAMETERS

(71) Applicant: Berlin Heart GmbH, Berlin (DE)

(72) Inventors: Sebastian Kallenbach, Kassel (DE); Hendryk Richert, Berlin (DE); Martin Grasse, Gosen-Neu Zittau (DE); Thaddäus Bautze, Berlin (DE); Oliver Peters, Berlin (DE)

(73) Assignee: Berlin Heart GmbH, Berlin (DE)

( * ) Notice: Subject to any disclaimer, the term of this patent is extended or adjusted under 35 U.S.C. 154(b) by 763 days.

(21) Appl. No.: 16/639,017

(22) PCT Filed: Aug. 14, 2018

(86) PCT No.: PCT/EP2018/072070
§ 371 (c)(1),
(2) Date: Feb. 13, 2020

(87) PCT Pub. No.: WO2019/034670
PCT Pub. Date: Feb. 21, 2019

(65) Prior Publication Data
US 2020/0222606 A1 Jul. 16, 2020

(30) Foreign Application Priority Data
Aug. 17, 2017 (EP) .................................. 17186563

(51) Int. Cl.
*G08B 21/04* (2006.01)
*A61M 60/178* (2021.01)
(Continued)

(52) U.S. Cl.
CPC ........ *A61M 60/531* (2021.01); *A61M 60/178* (2021.01); *A61M 60/237* (2021.01);
(Continued)

(58) Field of Classification Search
USPC .... 340/539.12, 538.12, 538.15, 539.22, 544, 340/555, 576, 636.11, 636.15, 10.34,
(Continued)

(56) References Cited

U.S. PATENT DOCUMENTS 3,672,352 A * 6/1972 Summers ............. A61B 5/0031
607/33
8,613,608 B2 * 12/2013 Ree ........................ F04C 2/1071
418/160
(Continued)

FOREIGN PATENT DOCUMENTS

CN 101253332 A 8/2008
CN 2 330 405 A1 6/2011
(Continued)

OTHER PUBLICATIONS

International Search Report, issued in International Application No. PCT/EP2018/072070, dated Oct. 26, 2018, pp. 1-2, European Patent Office, Rijswijk, Netherlands.
(Continued)

*Primary Examiner* — Daniel Previl
(74) *Attorney, Agent, or Firm* — Crowell & Moring LLP (57) ABSTRACT

A pump is provided for conveying body fluids, in particular blood, wherein the pump has a pump housing and a rotor mounted in the pump housing. The rotor comprises at least one sensor for detecting flow and/or movement parameters. Also provided is a method for operating the pump.

20 Claims, 4 Drawing Sheets

(51) Int. Cl.
  *A61M 60/237* (2021.01)
  *A61M 60/422* (2021.01)
  *A61M 60/523* (2021.01)
  *A61M 60/531* (2021.01)
  *A61M 60/538* (2021.01)
  *A61M 60/806* (2021.01)
  *A61M 60/873* (2021.01)
  *A61M 60/148* (2021.01)

(52) U.S. Cl.
  CPC ........ *A61M 60/422* (2021.01); *A61M 60/523* (2021.01); *A61M 60/538* (2021.01); *A61M 60/806* (2021.01); *A61M 60/873* (2021.01); *A61M 60/148* (2021.01); *A61M 2205/0294* (2013.01); *A61M 2205/332* (2013.01); *A61M 2205/3331* (2013.01); *A61M 2205/3334* (2013.01); *A61M 2205/50* (2013.01); *A61M 2205/82* (2013.01); *A61M 2205/8237* (2013.01); *A61M 2230/50* (2013.01); *A61M 2230/63* (2013.01)

(58) Field of Classification Search
  USPC .......... 340/10.1, 572.1, 657; 250/338.8, 250, 250/251, 252.1, 271, 281, 301, 253; 455/509, 517, 450, 451, 73; 73/146, 431, 73/577, 579, 582, 760, 781, 786, 788, 73/789, 826, 828; 29/623.5, 825; 324/126, 649, 76.11; 370/345, 466; 429/162, 1, 2, 3, 4, 5, 6, 7, 8, 9, 10, 11, 429/400, 48, 47, 49, 50, 53, 57, 61, 65, 429/66, 67, 71, 72; 418/48, 152, 160, 418/161, 171, 179, 182, 68, 1, 2, 3, 4, 5, 418/14, 15, 16, 32, 33, 39, 40, 45; 123/193.2, 1 R, 2, 200; 310/90, 90.5, 310/300, 1, 10, 800, FOR. 000, FOR. 101, 310/FOR. 100, DIG. 2, DIG. 3, DIG. 6; 366/273, 1, 69, 108, 101, 129, 131, 366/137.1, 138, 139, 140, 141, 143, 142, 366/144, 150.1, 184; 378/123, 127, 130, 378/133, 141, 1, 91, 119, 145, 162, 167, 378/189, 193; 403/292, 379.3, 1, 2, 5, 3; 416/105, 158, 1, 2, 3, 4, 5, 6, 7, 9; 417/211.5, 356, 423.12, 423.7, 353, 354, 417/423.1, 63, 1, 48, 52, 53, 56, 61, 62, 417/64, 65, 199.1, 207, 210, 211, 212, 417/225, 228, 229, 234, 236, 238, 240, 417/242, 243, 244, 269, 274, 278, 279, 417/313, 312, 314, 315, 316, 319, 320, 417/321, 425, 426, 430, 432, 434, 435, 417/436, 437, 572, 900, 901, 902, 903, 417/904, FOR. 00, DIG. 1; 464/102; 60/605.1; 604/151, 500, 1, 890.1, 4.01, 604/7, 8, 11, 540, 19, 317, 403, 900, 901, 604/902, 903, 904, 905, 906, 907, 908, 604/909, 910, 911, 912, 913, 914, 915, 604/FOR. 000, FOR. 100; 623/3.13, 3.24, 623/1.1, 2.1, 3.1, 4.1, 7, 9, 10; 318/114, 318/128, 649; 361/699, 1, 139, 211, 212, 361/225, 230, 236, 245, 247, 267, 268, 361/271, 600, 500, 437, FOR. 000
  See application file for complete search history.

(56) References Cited

U.S. PATENT DOCUMENTS

| | | | |
|---|---|---|---|
| 9,074,912 B2* | 7/2015 | Hassel | H02K 11/20 |
| 9,764,072 B2* | 9/2017 | Wiesener | A61M 60/894 |
| 10,290,209 B2* | 5/2019 | Larcher | G08G 1/14 |
| 2004/0152944 A1 | 8/2004 | Medvedev et al. | |
| 2012/0170567 A1* | 7/2012 | Lahner | H04W 74/02 370/345 |
| 2013/0251502 A1 | 9/2013 | Ketcham et al. | |
| 2013/0284928 A1* | 10/2013 | Frey | G01N 33/0027 250/338.5 |
| 2014/0066691 A1* | 3/2014 | Siebenhaar | A61M 60/585 600/16 |
| 2014/0072459 A1* | 3/2014 | Kalavsky | F04D 29/051 310/90 |
| 2014/0211810 A1* | 7/2014 | Heinrich | H04L 69/08 370/466 |
| 2015/0268069 A1* | 9/2015 | Peters | G01D 11/24 73/431 |
| 2016/0045841 A1* | 2/2016 | Kaplan | C01B 32/05 429/49 |
| 2016/0181059 A1* | 6/2016 | Vystavel | H01J 37/16 250/442.11 |
| 2016/0263300 A1 | 9/2016 | Wiesener et al. | |

FOREIGN PATENT DOCUMENTS

| | | |
|---|---|---|
| CN | 102741677 A | 10/2012 |
| WO | WO 2011/054545 A1 | 5/2011 |
| WO | WO 2011/076440 A1 | 6/2011 |
| WO | WO 2012/149946 A1 | 11/2012 |
| WO | WO 2012/150045 A2 | 11/2012 |
| WO | WO 2015/059158 A1 | 4/2015 |
| WO | WO 2015/160942 A1 | 10/2015 |
| WO | WO 2016146748 A1 | 9/2016 |
| WO | WO 2017102164 A1 | 6/2017 |

OTHER PUBLICATIONS

First Office Action for China Application No. 201880052192.7 dated Jul. 4, 2022 (Chinese language only) (11 pp.).

* cited by examiner

PUMP HAVING A ROTOR SENSOR FOR DETECTING PHYSIOLOGICAL PARAMETERS, FLOW PARAMETERS, AND MOVEMENT PARAMETERS

CROSS-REFERENCE TO RELATED APPLICATIONS

This application is a 371 nationalization of international patent application PCT/EP2018/072070 filed Aug. 14, 2018, which claims priority under 35 USC § 119 to European patent application 17186563.7 filed Aug. 17, 2017. The entire contents of each of the above-identified applications are hereby incorporated by reference.

TECHNICAL FIELD

The invention relates to a pump for delivering body fluids, in particular blood, wherein the pump comprises a pump casing and a rotor which is mounted in the pump casing.

DETAILED DESCRIPTION

The invention lies in the field of engineering and in particular precision engineering and electrotechnology and can be applied particularly advantageously to the field of medical technology.

It is particularly in the medical field that pumps for delivering fluids in the body of a patient present high technical demands. In this context, blood pumps which suck blood at a first location in the blood vessel system of a patient and deliver this to a second location within or outside the blood vessel system are known. Typically, the mentioned pumps comprise a pump casing and a rotor which is mounted in the pump casing. Hereby, as a rule, the rotor is activated by a control device which is provided in the pump casing. Nowadays, in a blood pump, it is possible to measure and to estimate e.g. the blood pressure, the temperature, the acceleration of the pump casing and the blood flow within the pump by way of suitable sensors. The rotor can then be activated accordingly, on the basis of these measured or estimated values. A feedback mechanism is therefore used, in order to activate (control) the rotor in a precise as possible manner and in accordance with the requirements.

The publication WO 2015/059158 A1 describes e.g. a method for the operation of such a pump device.

It would be desirable to develop a pump for delivering body fluids, concerning which the measurement of the flow forces and turbulence of the blood flow is improved for recognising the pump performance capability. In particular, it would be desirable to be able to better predict or recognise one or more of the following parameters: condition of the pump, clots on the rotor and in the region of the pump, condition of the rotor mounting and pump service life.

Accordingly, the invention relates to a pump for delivering body fluids, in particular blood, wherein the pump comprises a pump casing and a rotor which is mounted in the pump casing.

The rotor comprises at least one sensor for detecting physiological parameters and/or physical parameters and/or flow parameters and/or movement parameters. Hereby, the physiological parameters and/or physical parameters, flow parameters or movement parameters can be for example speed, pressure, temperature, rotation speed, angular speed, acceleration, oxygen content, $CO_2$ content and/or pH-value of the body fluid; and/or position, speed, pressure, temperature, rotation speed, operating state, mechanical stress, deformation, wear, surface parameters, surface conductance, thermal resistance and capacitance, nature, angular speed and/or acceleration of the rotor and/or of the pump. In particular, the sensor can be designed to detect changes or deviations of the mentioned flow or movement parameters with respect to predefined values, e.g. setpoints. The sensor can be designed e.g. to detect deviations of a rotation of the rotor about a rotation axis. In an embodiment, optical or radiological imaging methods can also be applied with the sensor. The mentioned parameters can be detected by the sensor, in particular during the pump operation or on rotating the rotor.

In a variant, the sensor is e.g. an acceleration sensor, a gyroscope, a force sensor, a flow sensor, an oxygen sensor, a $CO_2$-sensor, a proximity sensor, a light sensor, a position sensor, a pressure sensor, a temperature sensor, a magnetic field sensor (e.g. a coil) or a pH-sensor. The sensor can also be an RFID sensor (radio-frequency identification sensor). The rotor can comprise a multitude of sensors, e.g. 2, 3, 4, 5, 6, or even more than 6.

In one embodiment of the invention, the at least one sensor is arranged on the rotor or in the rotor or within the rotor. Until now, in the state of the art, sensors have been attached to the static pump casing. For example, in the state of the art, an arrangement of sensors is provided at a rotor of a blood pump, in order to detect a position of the rotor and to detect an operating state of the rotor. Here however, the sensors are not assembled on the rotor or in the rotor itself. On account of the weight of the rotor which as a rule is comparatively low in comparison to a weight of the pump casing, the sensor which is arranged on or in the rotor can detect e.g. the smallest of deviations from the setpoints. For this reason, a sensitive measuring instrument can be provided with the pump.

Since the rotor rotates during the operation of the pump, a wiring of the rotor to an external energy source for the sensor, provided e.g. on the pump casing or in an external device which is not arranged in the patient body, is often undesirable.

The sensor itself can be energy self-sufficient, i.e. in this case the sensor itself is capable of using energy from its environment for its operation. In this case, the sensor can be e.g. a sensor coil, a piezoelectric sensor element or a sensor photodiode.

Alternatively or additionally, the rotor can also include an energy store, such as for example a capacitor, a chargeable accumulator or a battery for the energy supply of the sensor.

In a further embodiment, the rotor comprises an energy converter (also called transducer) for the wireless energy supply of the sensor. In the context of the present document, wireless means that the sensor and/or rotor are not wired to static, non-moving components of the pump casing and that the sensor as a rule is only wired to components on the rotor. By way of this, the rotor can rotate in an uninhibited manner during the operation of the pump and a wearing of the components is reduced. In particular, the energy transducer is designed to convert energy of an energy source which is not connected to the rotor, into an energy form which can be utilised for the sensor.

In particular, the aforementioned energy store can be charged by an electrical current which is produced in the energy transducer. The energy store can be connected to the at least one sensor for its supply of electricity.

The pump can further comprise an energy source for the sensor. For example, the energy source is designed to transfer energy onto the energy transducer in a wireless manner. The energy source and the energy transducer are typically designed in a manner such that energy which is provided by the energy source can be converted in the energy transducer of the rotor. The energy which is provided by the energy source then as a rule is converted by the energy transducer into an energy form which is necessary for the operation of the sensor, i.e. into electrical current. The energy source can therefore be energetically coupled to the energy transducer. The energy source can be provided e.g. in the pump casing. Furthermore, the energy source is usually not electrically or mechanically connected to the rotor. The energy source does not necessarily need to be a constituent of the pump casing or of the pump, it can be provided e.g. in a separate device which is arranged within or outside the patient body, or form a separate device.

The energy transducer can be e.g. a rotor coil, a piezoelectric rotor transducer or a photodiode. The energy source can then be a stator coil, a light source or a sound source, for an energetic coupling to the rotor coil, the photodiode or the piezoelectric rotor transducer. Several equal or different types of energy sources and several equal or different types of energy transducers can be provided simultaneously.

The rotor coil can be designed in a manner such that a voltage can be induced in the rotor coil given a rotation of the rotor. The rotor coil therefore is typically designed to produce an electrical current for the operation of the at least one sensor, given a rotation of the rotor. This is effected e.g. by way of a temporally changing magnetic field variation (e.g. by way of motor detent torques) in the rotor coil. For this purpose, one can envisage the pump casing comprising at least one permanent magnet in the region of the rotor for the induction of the voltage in the rotor coil. A voltage is therefore induced in the rotor coil by way of the rotation of the rotor and the rotor coil in relation to the pump casing and the permanent magnet. The permanent magnet and/or the permanent magnets is/are preferably arranged in the pump casing in a manner such given a predefined rotation speed of the rotor, the permanent magnet or the permanent magnets induce a predefined voltage course in the co-rotating rotor coil. A frequency of the alternating voltage which is induced in the rotor coil depends on the number of permanent magnets as well as on the rotation speed of the rotor.

Alternatively or additionally, one can envisage the pump casing comprising a stator coil as an energy source for the sensor, wherein a predefined voltage or a predefined temporal voltage course in the rotor coil can be induced by way of subjecting the stator coil to current. Typically, in actively magnetically mounted blood pumps, permanent magnets are integrated at least in the rotor, whereas permanent magnets and coils with magnetic return paths are located in the pump casing. An (alternating) voltage is therefore applied to these coils in the pump casing for the mounting and rotation of the rotor. According to the aforedescribed design, this voltage can now be modulated with a predefined voltage so that a predefined voltage is induced in the rotor coil. Energy can therefore be transferred wirelessly by way of the rotor coil and preferably the stator coil. For this, it is advantageous if the stator coil encompasses the rotor at least in regions. A frequency of the voltage which is induced in the rotor coil can differ from the rotation frequency of the rotor. E.g. the frequency of the alternating voltage which is induced in the rotor coil can be smaller or larger than the rotation frequency of the rotor. The frequency of the voltage induced in the rotor coil can be e.g. larger than 100 Hz, larger than 150 Hz or larger than 200 Hz.

It is to be noted that dimensions and inductance of the rotor coil are typically chosen in accordance with the design of the energy transmission path.

In a further embodiment, the energy transducer is a piezoelectric rotor transducer. The piezoelectric rotor transducer is designed to convert energy of a mechanical pressure wave, such as e.g. a sound wave or an ultrasonic wave, into electrical current. The mechanical pressure waves are typically absorbed by the piezoelectric transducer, by which means a piezoelectric crystal in the piezoelectric transducer deforms. The mentioned deformation produces an electrical current which is used by the sensor. One advantage of piezoelectric transducers compared to coils is the fact that the mechanical pressure waves can propagate particularly well in the body of a patient. In particular, they are not shielded by a metallic pump casing. By way of this, one can select the location of the piezoelectric transducer on the rotor or in the rotor in a relatively flexible manner. Furthermore, there is a flexibility concerning the choice of materials, e.g. of the casing and of the rotor, and concerning the selection of the location of the energy source. The energy source for the piezoelectric rotor transducer can be e.g. a sound source, in particular an ultrasound source which is arranged in the pump casing or outside the pump casing. The sound source can be for example a loudspeaker or a piezoelectric element. The sound source can be operated in a stationary or pulsed manner. In a further design, the pump comprises a piezoelectric pump transducer for a piezoelectric coupling to the piezoelectric rotor transducer.

Basically e.g. a light source can also be provided as an energy source and a photodiode or solar cell which are provided on the rotor can be provided as an energy transducer. The selection of a wavelength which is to be emitted by the light source depends on the absorption behaviour of the body fluid and on the efficiency of the photodiode or solar cell. The light source and the photodiode or solar cell should be designed to emit or absorb light which is permeable for body fluids, in particular blood, and to convert it into an energy form which can be used by the sensor. A suitable wavelength of the light which is emitted by the light source can be for example at least 600 nm, preferably at least 650 nm, in particular at least 700 nm. The wavelength of the light which is emitted by the light source can be maximally 1500 nm, or maximally 1300 nm. With large wavelengths, the efficiency of common photodiodes or solar cells can rapidly diminish. E.g. an LED, a laser or a lamp are considered as a light source. The light source can be operated in a stationary or pulsed manner.

Typically, the pump comprise a wireless communication interface between the sensor and at least one further component of the pump or of a pump device (see below), such as e.g. a control and processing unit (see below). By way of this, data or signals of the sensor can be transmitted in a wireless manner to at lasts one further component. The wireless communication of the communication interface can be effected e.g. via radio signals, an inductive coupling, optical signals, acoustic signals or other suitable signals. The communication interface can comprise e.g. one or more communication units.

The information transmission at the communication interface can be effected in a separate manner or together with the energy transmission. Variants and combinations include e.g. the information transmission by way of modulation of the energy uptake, a variable reflection factor, a variable delay between an incoming and outgoing energy pulse and/or the formation of an oscillation circuit which utilises incoming and outgoing coupling interfaces, in order to accommodate the components which determine the frequency and/or phase, in the rotor.

In one embodiment, the pump comprises a first communication unit for the wireless transmission of sensor signals of the sensor. The first communication unit can be arranged on or in the rotor. In one variant, the energy transducer is simultaneously designed as the first communication unit. By way of this, the number of components which are to be installed can be kept low. One can alternatively envisage the first communication unit differing from the energy transducer. For transferring the sensor signals, the first communication unit can comprise a suitable transmitting unit for transmitting signals, such as an antenna, a light source, a coil or a sound source. Optionally, the first communication unit on the rotor can additionally comprise a receiving unit for receiving signals. For example, the first communication unit comprises e.g. an antenna for sending and/or receiving radio signals. The first communication unit can transfer the data and/or signals of the sensors to the second communication unit (see below) typically in intervals of 10 ms up to 100 ms.

Depending on the design of the pump, the pump casing can comprise a read-out unit for wirelessly reading out the at least one sensor. In this case, one can make do without the aforementioned first communication unit.

A pump device is also put forward by the invention. The pump device comprises a previously mentioned pump and a control and processing unit. The control and processing unit is preferably designed to evaluate sensor signals of the at least one sensor and to activate the pump on the basis of the sensor signals. In order to create a compact as possible system, the control and processing unit can be provided in the pump casing. However, it can also be provided as a separate unit. The pump can be implantable or implanted e.g. in a body of a patient. In one embodiment, the control and processing unit can be located within or outside the body of the patient. As already described, the control and processing unit is alternatively an integral constituent of the implanted pump.

The control and processing unit can comprise a second communication unit for the wireless communication with the first communication unit. For this, a suitable communication channel or a communication interface is provided between the two communication units. The first communication unit is preferably designed to transmit the sensor data and/or the sensor signals to the second communication unit. For this, the second communication unit is preferably designed to receive the sensor data and/or the sensor signals. In a further embodiment, the second communication unit is configured to transmit data to the first communication unit and the first communication unit is configured to receive data from the second communication unit.

If the aforementioned reading-out device is provided, then this can be connected to the control and processing unit for transmitting the sensor signals.

The control and processing unit can be designed to evaluate or process signals or data of the aforementioned sensor or several of the aforementioned sensors. The control and processing unit can comprise a microcontroller, a processor, a microprocessor and/or a digital signal processor, for processing and/or evaluating the signals and/or the data of the aforementioned sensors. Hereby, a digital signal processor (DSP) can be designed for a continuous processing of digital signals, for example digital signals of one or more of the aforementioned sensors.

Furthermore, the control and processing unit can comprise one or more memories, such as e.g. random access memory (RAM), read only memory (ROM), a hard drive, a magnetic storage medium and/or an optical drive. A program can be stored in the memory, e.g. software for processing or working through the data and/or the signals of a sensor or of several of the aforementioned sensors.

The control and processing unit can further be designed to activate the pump and/or the energy source and/or the at least one sensor and/or the rotor and/or other devices and/or to carry out a certain action, on the basis of or depending on the sensor data or sensor signals.

The control and processing unit can be designed e.g. to activate the energy source, such as e.g. the stator coil, in a manner such that a predefined energy quantity or power is taken up by the energy transducer, such as e.g. the rotor coil, and the energy transducer provides a predefined quantity of energy or power for the sensor.

In one variant, the rotor coil can be designed simultaneously as an energy transducer and as a communication unit. In this case, the rotor coil assumes the energy transmission as well as the data transmission.

The pump can comprise a coding unit which is designed to code signals of the sensor and to lead the coded signals further to the communication unit, such as the rotor coil. The coding unit is typically likewise located on the rotor or in the rotor.

In a further embodiment, one can envisage the rotor coil being designed simultaneously as a sensor and first communication unit. In this case, one can make do without an additional energy transducer. A second coil which is arranged on the pump casing can then measure changes in the magnetic field which are induced by the rotor coil and lead them further to the control and processing unit.

The pump casing can be designed as a plastic casing, a ceramic casing or metal casing. The pump casing can also comprise a combination of the aforementioned materials (plastic, ceramic and/or metal). The material selection for the pump casing can be influenced by the selection of the sensor, of the energy transducer, of the energy source and of the first communication unit.

Typically, a weight of the pump in total is at least 50 g and/or 250 g at the most. The weight of the rotor of an axial pump is 25 g at the most, preferably 15 g at the most. Furthermore, the weight of the rotor of a radial pump is 40 g at the most, preferably 30 g at the most. Furthermore, the rotor can be mounted in an actively magnetic or mechanical or hydrodynamic manner.

A method for operating the previously described pump for delivering body fluids, in particular blood, is also put forward by the invention, wherein the pump comprises a pump casing and a rotor which is mounted in the pump casing.

The method comprises at least the step: detecting physiological parameters and/or physical parameters and/or flow parameters and/or movement parameters by a sensor which is arranged on the rotor or in the rotor. For example, the mentioned parameters are detected during the pump operation or on rotating the rotor.

Here, it is to be emphasised that the features which are described in the context of the pump or the pump device can also be claimed for the method.

The invention is hereinafter explained further by way of attached figures. Recurring elements are hereinafter provided with the same reference numerals.

Figure 1:
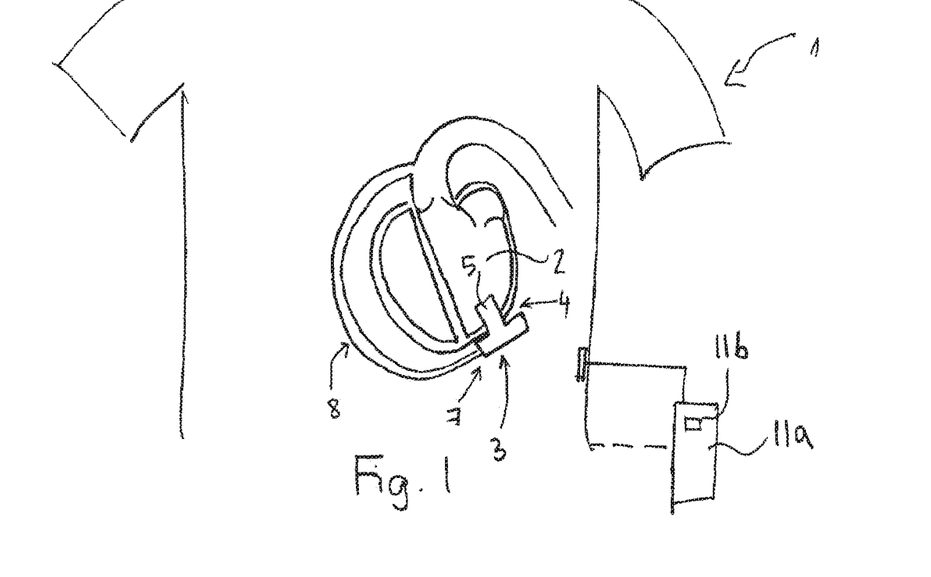
FIG. 1 shows schematically, the representation of a patient body with a heart catheter pump which is introduced into a heart chamber via the aorta.

FIG. 1 schematically shows a patient body 1 with a heart chamber 2, into which a blood pump 3 is introduced. Herein, the blood pump 3 is connected to the apex 4 of the heart ventricle. In the shown example, the pump 3 is connected to the left ventricle of the heart, i.e. the pump 3 is a left ventricular assist device or also LVAD.

Figure 2:
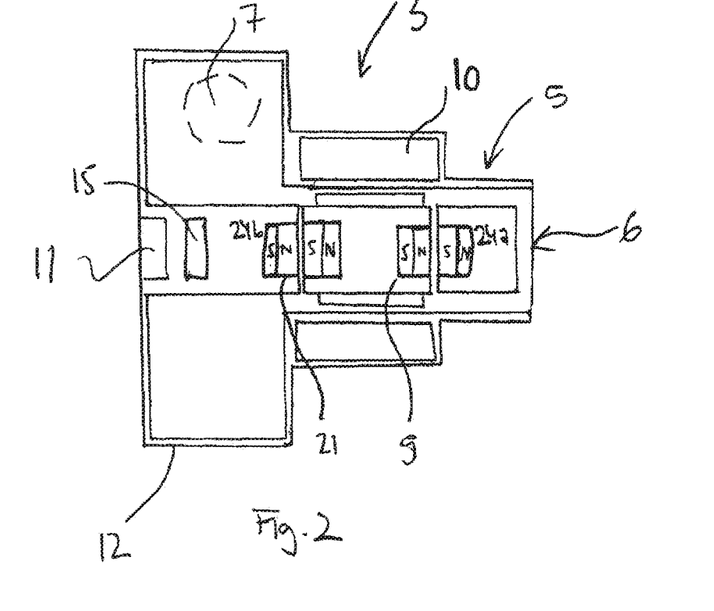
FIG. 2 shows in an enlarged representation, a heart catheter which is with a heart pump and which is introduced through an aortic arch.

The blood pump 3 is represented in an enlarged manner in FIG. 2. An inlet piece 5 of the blood pump 3 which is introduced directly into the apex 4, in the present embodiment example comprises a suction opening 6, through which the blood is sucked. In the present embodiment example, the blood is delivered by way of an axial blood pump 3 with a tangential outlet 7. The outlet 7 is connected to the aorta by way of a cannula 8 or a hose-like object. Alternatively, the outlet 7 can be connected to the pulmonary artery (given an RVAD) or to the shoulder artery. A rotor 9 which is provided with a spiral 14 is located in the inlet piece 5, said rotor being able to be brought into rotation via a stator 10 of the blood pump 3 and hence sucking the blood into the suction openings 6. One example of such a blood pump can be derived from WO 2012/149946 A1, WO 2011/054545 A1 or WO 2012/150045 A1 or in WO 2015/059158 A1, whose disclosures are adopted to the full extent into the present application by way of reference.

Further examples of suitable blood pumps are the blood pumps of the EXCOR® and INCOR® construction series of Berlin Heart GmbH (Ltd.), Germany. Concerning the use of these blood pumps, the pumps are connected to the heart via cannulas, so that the suction element can be the pump itself as well as the inlet of the cannula, said cannula connecting the pump to the heart.

The blood pump 3 comprises a control device 11, 11b or 31 for the control of the rotor 9, said control device being able to be arranged for example within a pump casing 12 or in a separate, additional casing 11a which is arranged within or outside the body. The control is usually effected by way of an automatic feedback loop.

Figure 3:
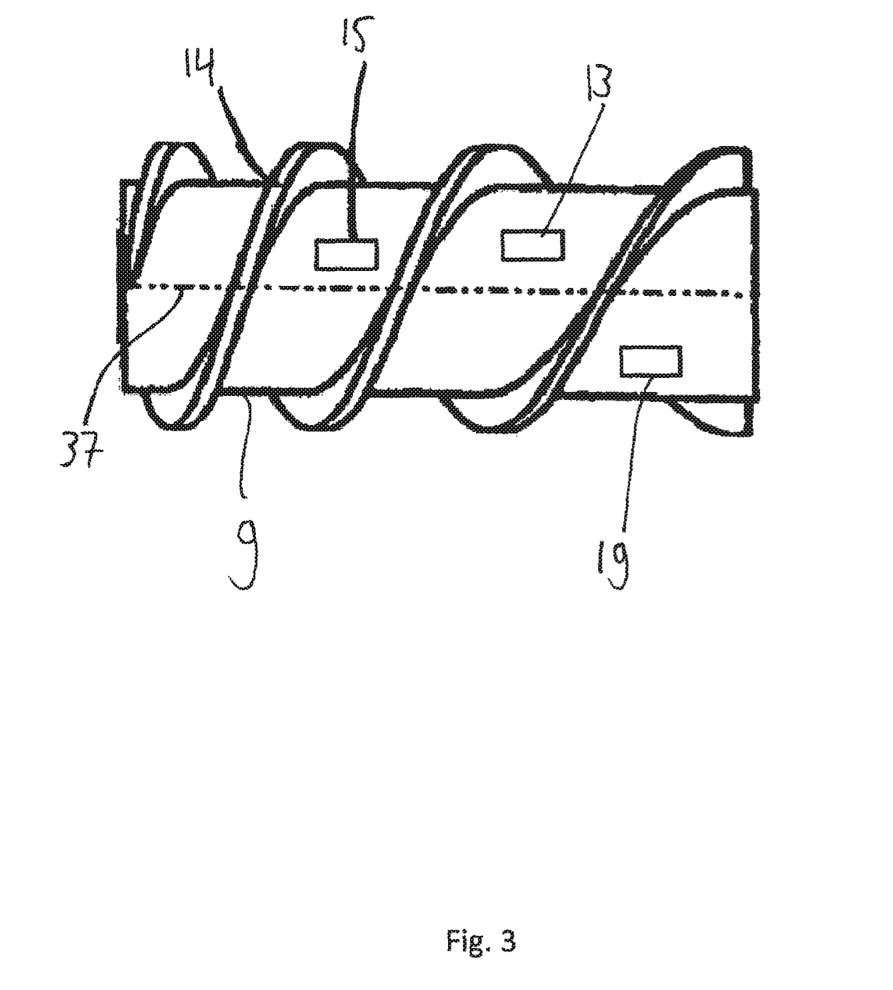
FIG. 3 shows a view of an axial rotor.

FIG. 3 shows a view of the rotor 9 with the spiral 14. In particular, the rotor 9 of FIG. 3 can be applied in the pump 3 of FIGS. 1 and 2. The rotor 9 which is mounted in the pump casing 12 is mounted in an actively magnetic manner and comprises at least one sensor 15 for detecting flow and movement parameters. Neodymium-iron-boron magnets are located in the rotor 9, whereas passive magnets 21 are located in the pump casing 12 and active magnet coils in the stator 10 for the drive and the axial-radial mounting of the rotor 9. The rotor 9 forms the only moving part in the pump 3.

The rotor 9 comprises at least one sensor 15. As is indicated in the FIGS. 4 and 5, several sensors 15, 16 and 17 can also be arranged on or in the rotor 9. By way of evaluating the sensor signals, one can obtain information on the condition of the pump 3, on arising clots on the spiral 14 of the rotor 9 or in the pump region and on the condition of the mounting of the rotor 9. Furthermore, by way of this one can make a prediction concerning the service life of the pump. For this, the sensors 15, 16 17 can be designed to detect physiological parameters, physical parameters, movement and/or flow parameters. Possible parameters which are to be detected by the sensor 15, 16, 17 are specified further above. For example, the sensors 15, 16, 17 can be designed to detect deviations of a rotation 9 about a rotation axis 37.

Various sensors are considered as a sensor 15 or sensors 15, 16, 17. For example, the sensor 15 or the sensors 15, 16, 17 can be an acceleration sensor, a gyroscope, a force sensor, a flow sensor, an oxygen sensor, a $CO_2$ sensor, a proximity sensor, a light sensor, a position sensor, a pressure sensor, a temperature sensor, a magnetic field sensor, a coil, an RFID-sensor or a pH-sensor. Several different types of sensors 15, 16, 17 can also be provided. The sensor 15, 16, 17 can be designed for example as a coil. The at least one sensor 15 is connected to a first communication unit 19 which is dealt with in more detail further below.

The rotor 9 comprises one or more energy converters 13 (sometimes also called transducers) for the energy supply of the sensor 15 or of the sensors 15, 16, 17. The energy transducer 13 can be designed e.g. as a rotor coil, photodiode/solar cell or as a piezoelectric transducer. The sensor 15 or the sensors 15, 16, 17 can therefore obtain their energy in a wireless manner from an energy source 20 which is not arranged on the rotor 9, by way of the energy transducer 13 which is arranged on the rotor 9. The rotor 9 can comprise a battery 18 for the supply of electricity to the sensors 15, 16, 17, in order to improve the energy supply of the sensors 15, 16, 17 or to ensure a constant supply of energy, wherein the battery 18 can be charged by way of electrical current which is produced in the energy transducer 13. Alternatively to the energy transducer 13, a battery or a chargeable accumulator for an energy supply of the sensor 15, 16, 17 can also be arranged on or in the rotor 9. In an embodiment, the sensor 15, 16, 17 is energy-autonomous. In this case, the sensor 15, 16, 17 can be e.g. a sensor coil, a piezoelectric sensor element or a sensor photodiode.

Given a design of the energy transducer 13 as a rotor coil, the pump casing 12 and the rotor coil can be designed in a manner such that a voltage can be induced in the rotor coil given a rotation of the rotor. This can be accomplished on the part of the pump casing 12 e.g. by way of a passive permanent magnet, but one can also provide an active stator coil which is designed to induce a predefined voltage in the rotor coil, in order to cover the energy requirement of the sensor 15, 16, 17. The stator coil can be arranged in the sensor 10 and completely encompass the rotor 9.

Given a design of the energy transducer 13 as a piezoelectric pump transducer, this is designed to convert mechanical pressure waves, in particular ultrasound waves, into electrical energy. If a mechanical pressure wave hits the piezoelectric transducer 13, a piezoelectric crystal deforms in the transducer, by which means a current is generated in the piezoelectric transducer. A further piezoelectric transducer or another type of sound source can be provided preferably in the pump casing 12, for providing the mechanical pressure waves.

Alternatively or additionally, the energy transducer 13 can also be a solar cell or photodiode which converts light energy into electrical energy.

Figure 4:
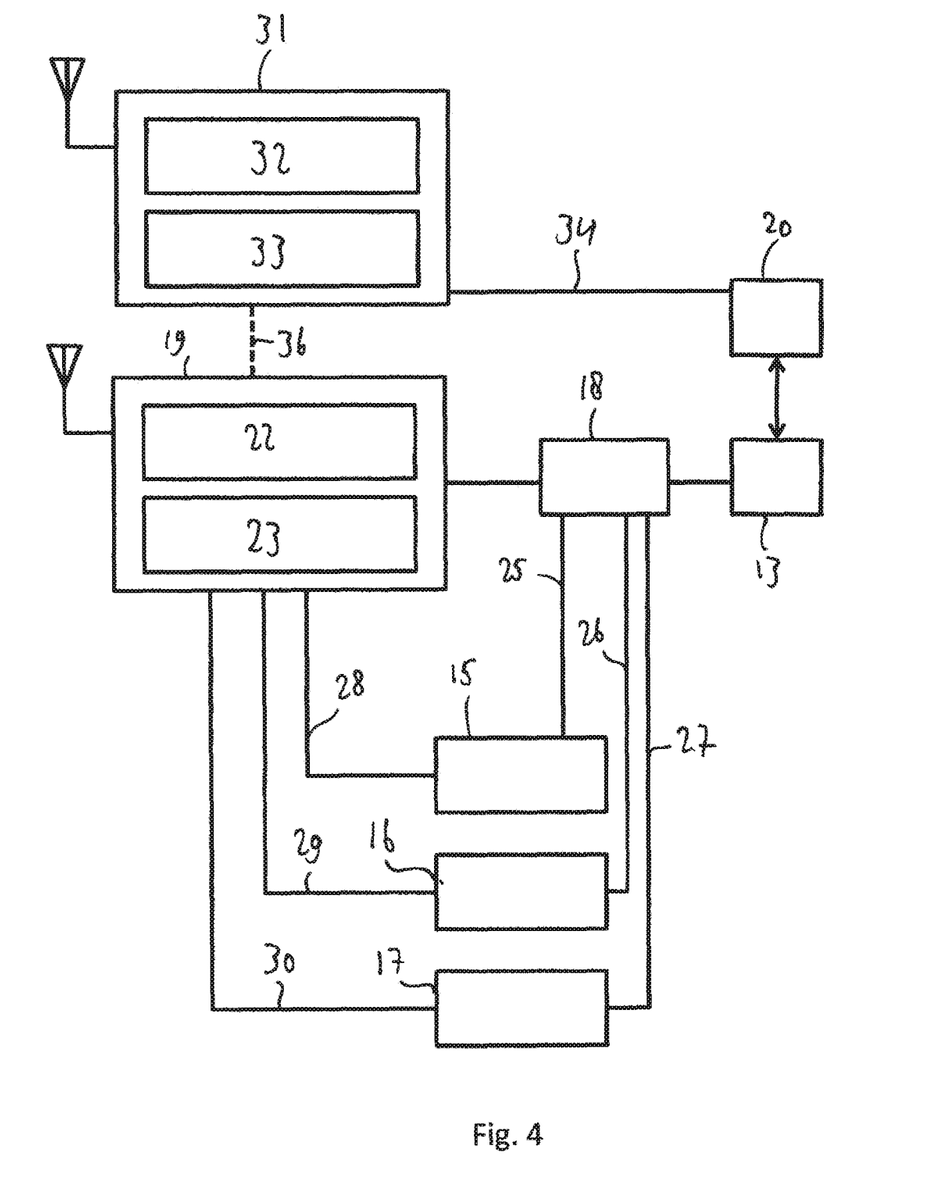
FIG. 4 shows a schematic representation of a rotor circuit.

FIG. 4 shows an example of the circuiting of the componentries which are located on and in the rotor 9 as well as in the pump casing 12. An energy source 20 which provides energy for the energy transducer 13 is shown in FIG. 4. Hereby, the energy source 20 is preferably arranged on the static pump casing 12, whereas the energy transducer 13 is provided on or in the rotor 9. The energy transducer 13 is connected to a battery 18 and/or to a rectifier 18. The battery 18 or the rectifier 18 ensure that the sensors 15, 16 and 17 can be supplied with a constant as possible direct voltage/direct current. For this, the battery 18 or the rectifier 18 are connected to the sensors 15, 16 and 17 via supply leads 25, 26 and 27 respectively. The sensors 15, 16, 17 are connected to the first communication unit 19 by way of communication leads 28, 29 and 30 respectively. The first communication unit 19 is also located on the rotor 9 or within the rotor 9. The first communication unit 19 comprises a transmitting and receiving module 22 as well as a digital/analog converter 23. The sensor signals are converted or coded into digital signals in the digital/analog converter and are led further to the transmitting and receiving module 22. The transmitting and receiving module 22 converts the digital signals of the sensors into data which is to be transmitted, and sends the data to be transmitted to a second communication unit 33 in a wireless manner via an antenna.

A control and processing unit 31 which can be identical to the control device 11 of FIGS. 1 and 2 is further shown in FIG. 4. The control and processing unit 31 comprises e.g. a rotor control and a second communication unit 33. The second communication unit 33 is wirelessly connected to the first communication unit 19 via communication channels 36. Although the communication unit 19 and the second communication unit 33 each have an antenna in FIG. 4, other means can also be provided for the wireless communication between the two communication units 19 and 33. Thus, a coil or a piezoelectric transducer may be provided in each of the two communication units 19 and 33 for the communication between the two communication units 19 and 33.

Figure 5:
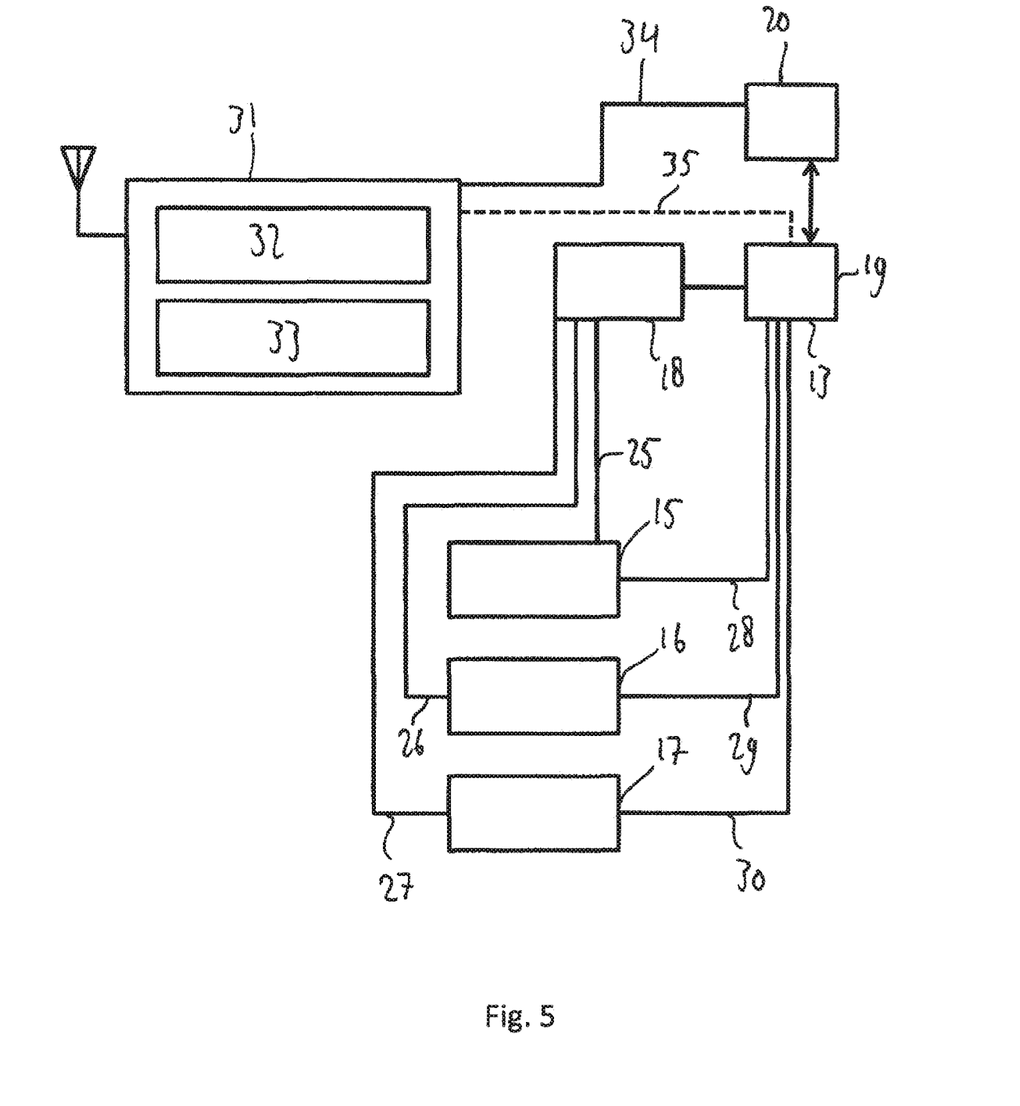
FIG. 5 shows a further schematic representation of a rotor circuit according to the invention.

The embodiment of FIG. 5 differs from the embodiment of FIG. 4 in that the energy transducer 13 of FIG. 5 is furthermore designed as a communication unit 19. The combined unit "energy transducer 13/first communication unit 19" is connected to the second communication unit 33 by way of a wireless communication channel 35. Furthermore, the sensors 15, 16, and 17 are connected to the combined unit "energy transducer 13/first communication unit 19" by way of communication leads 28, 29 and 30 respectively.

The combined unit "energy transducer 13/first communication unit 19" can be e.g. a coil which receives the energy from an energy source 20 which is designed as a stator coil. Given a suitable placement of permanent magnets in the pump casing 12, one can also make do without the energy source 20. The alternating voltage which is induced in the rotor coil is provided for the sensors 15, 16, 17 e.g. via the battery or rectifier 18. The measuring signals of the sensors 15, 16, 17 are converted into coded voltage signals in the sensors 15, 16, 17 and are led further to the combined unit "energy transducer 13/first communication unit 19" via the communication leads 28, 29, 30. Alternatively for this, one can also provide at least one separate coding unit. Magnetic field variations arise by way of the coded voltage signals in the coil of the combined unit "energy transducer 13/first communication unit 19", which in turn can be measured or read out by way of coils on the pump casing 12 which are designed as a second communication unit 33.

The combined unit "energy transducer 13/first communication unit 19" therefore not only ensures the energy transfer between the energy source 20 and the sensors 15, 16 and 17 but is also responsible for the transmission of the data or signals of the sensors 15, 16, 17 to the second communication unit 33.

In a preferred embodiment, the alternating voltage frequencies of the data transmission and of the energy transmission differ significantly, i.e. by more than e.g. 50%, so that there are no undesirable superimpositions and interfering signals. A frequency which is used for the data transmission should further e.g. be significantly greater than an average rotation frequency of the rotor 9, e.g. at least 2, 3, 5, 10 or 50 times as large. On the other hand, the frequency which is used for data transmission should be small enough, in order to keep the effect of the Faraday cage of the (metallic) pump casing 12 as low as possible.

As described above, the information transmission at the communication interface can therefore be effected separately or together with the energy transmission. Further embodiments comprise e.g. the information transmission by way of modulation of the energy uptake, a variable reflection factor, a variable delay between in incoming and outgoing energy impulse and/or the formation of an oscillation circuit which utilises incoming and outgoing coupling interfaces, in order to accommodate the components which determine the frequency and/or phase, in the rotor.

Concerning the radio connection, e.g. ISM bands (Industrial, Scientific and Medical bands at about ~6.7 MHz, ~13.5 MHz, ~27 MHz, ~40 MHz, ~433 MHz, ~902 MHz, ~2.4 MHz, ~5.8 GHz) as well as the range of 120 kHz to 150 kHz are considered for the communication.

If the transmission path is completely shielded, then other frequencies can also be used, since the pump as a system does not produce high-frequency emissions.

In particular, low frequencies are also considered for the energy supply. These can lie e.g. in the range of 10 Hz to 100 kHz.

Furthermore, in FIG. 5 as well as FIG. 4, the energy source 20 is connected to the control and processing unit 31 by way of a communication lead 34. In other words, the control and processing unit 31 also activates the energy source 20 in accordance with the energy requirements of the sensors 15, 16 and 17. Furthermore, the control and processing unit 31 in particular is designed to evaluate sensor signals of the at least one sensor 15, 16, 17 and to activate the pump 3 or the rotor 9 on the basis of the sensor signals.

In a further variant, the rotor 9 comprises a sensor 15 which is designed as a rotor coil. Currents which are induced in this rotor coil can then be read out by a read-out device which is arranged on the pump casing 12, e.g. by the aforementioned stator coil, and be led further to the control and processing unit 31. In this variant, one can make do without the energy transducer 13.

The pump casing 12 of the aforementioned embodiment examples can be a plastic casing, a ceramic casing or a metal casing. Although the pump 3 which is described above is designed as an axial pump, the pump 3 can also be designed as a radial pump. Depending on the design of the pump, a weight of the rotor is 15 g at the most (in the case of an axial pump) and a weight of the rotor of the radial pump is preferably 40 g at the most. The weight of the rotor 9 is much less than the weight of the complete pump 3 due to the fact that the weight of the pump 3 as a whole is at least 100 g and/or the most 250 g.

A method is also provided by the invention, said method comprising at least the following steps: detecting physiological parameters and/or physical parameters and/or flow parameters and/or movement parameters by way of a previously described sensor 15, 16, 17 which is arranged on the rotor 9 or in the rotor 9. The mentioned parameters can be detected e.g. during the pump operation or on rotation of the rotor.

Features which are only described in embodiment examples can be claimed individually or combined with one another.

The present invention further relates to the following aspects:

1. A pump for delivering body fluids, in particular blood, wherein the pump comprises a pump casing and a rotor which is mounted in the pump casing, wherein the rotor comprises at least one sensor for detecting physiological parameters and/or flow parameters and/or movement parameters.
2. A pump according to aspect 1, wherein the rotor comprises an energy transducer for the wireless energy supply of the sensor.
3. A pump according to aspect 2, comprising an energy source for the sensor, said energy source being designed to transmit energy to the energy transducer in a wireless manner, wherein the energy source and the energy transducer are designed in a manner such that energy which is provided by the energy source is converted in the energy transducer of the rotor into an energy form which is necessary for the operation of the sensor.
4. A pump according to aspect 2 or 3, wherein the rotor comprises an energy store, wherein the energy store is chargeable by way of electrical current which is produced in the energy transducer.
5. A pump according to one of the aspects 2 to 4, wherein the energy transducer is a rotor coil, a photodiode or a piezoelectric rotor transducer.
6. A pump according to aspect 5, wherein the pump casing and the rotor coil are designed in a manner such that a voltage can be induced in the rotor coil given a rotation of the rotor.
7. A pump according to one of the aspects 5 to 6, wherein the pump casing comprises at least one permanent magnet in the region of the rotor for the induction of the voltage in the rotor coil.
8. A pump according to one of the aspects 5 to 7, characterised in that the pump casing comprises a stator coil, wherein a predefined voltage in the rotor coil can be induced by way of subjecting the stator coil to current.
9. A pump according to aspect 8, characterised by a control and processing device which is connected to the stator coil and which is designed to activate the stator coil in a manner such that a predefined voltage is induced in the rotor coil.
10. A pump according to one of the aspects 5 to 9, wherein the pump comprises a sound source for an energetic coupling to the piezoelectric rotor transducer, or a light source for an energetic coupling to the photodiode.
11. A pump according to one of the preceding aspects with a communication unit for the wireless transmission of sensor signals of the sensor, wherein the communication unit is arranged on or in the rotor.
12. A pump according to aspect 2 and 11 with a rotor coil, wherein the rotor coil is designed as a first communication unit as well as an energy transducer.
13. A pump according to aspect 11 or 12, with a coding unit which is designed to code signals of the sensors and to lead the coded signals further to the communication unit.
14. A pump according to one of the preceding aspects, wherein the sensor is an acceleration sensor, a gyroscope, a force sensor, a flow sensor, an oxygen sensor, a $CO_2$ sensor, a proximity sensor, a light sensor, a position sensor, a pressure sensor, a temperature sensor, a magnetic field sensor, a coil, an RFID-sensor or a pH-sensor.
15. A pump device, comprising a pump according to one of the previous aspects and a control and processing unit, wherein the control and processing unit is designed to process and/or evaluate the sensor signals of the at least one sensor and to activate the pump (3) on the basis of the sensor signals.
16. A method for operating a pump according to one of the aspects 1 to 14 or a pump device according to aspect 15, with the step: detecting physiological parameters and/or flow parameters and/or movement parameters by a sensor which is arranged on the rotor or in the rotor.

LIST OF REFERENCE NUMERALS 1. patient body
2. heart chamber
3. blood pump
4. apex
5. inlet piece
6. suction opening
7. outlet
8. cannula
9. rotor
10. stator
11. control device
11a. external casing
11b. control device
12. pump casing
13. energy transducer
14. spiral
15. sensor
16. sensor
17. sensor
18. battery/rectifier
19. first communication unit
20. energy source
21. permanent magnet
22. transmitting and receiving module
23. digital/analog converter
24a. hub
24b. hub
25. supply lead
26. supply lead
27. supply lead
28. communication lead
29. communication lead
30. communication lead
31. control and processing unit
32. rotor control
33. second communication unit
34. communication lead
35. communication channel
36. communication channel
37. rotor axis

The invention claimed is:
1. A blood pump comprising:
a pump casing;
a rotor which is mounted in the pump casing;
a sensor mounted on the rotor and configured to detect a physiological parameter, a physical parameter, a flow parameter, and/or a movement parameter;
wherein the sensor is further configured to detect deviations of a rotation of the rotor about a rotation axis;
wherein the rotor comprises an energy transducer adjacent the sensor and configured to supply wireless energy to the sensor, or comprises an energy store adjacent the sensor and configured to supply energy to the sensor, or wherein the sensor is energy self-sufficient.

2. The blood pump of claim 1 further comprising an energy source for the sensor, said energy source configured to transmit energy to the energy transducer in a wireless manner, wherein energy transmitted by the energy source is convertible by the energy transducer of the rotor into an energy form which is necessary for operation of the sensor.

3. The blood pump of claim 1, wherein the rotor comprises the energy store, wherein the energy store is chargeable via electrical current produced in the energy transducer.

4. The blood pump of claim 1, wherein the rotor comprises the energy transducer, and the energy transducer is a rotor coil, a photodiode, or a piezoelectric rotor transducer.

5. The blood pump of claim 4, wherein the pump casing and the rotor coil are designed in a manner such that a voltage can be induced in the rotor coil by the rotation.

6. The blood pump of claim 4, wherein the pump casing comprises at least one permanent magnet in a region of the rotor for induction of a voltage in the rotor coil.

7. The blood pump of claim 4, wherein the pump casing comprises a stator coil, wherein a predefined voltage in the rotor coil can be induced by way of subjecting the stator coil to current.

8. The blood pump of claim 7, further comprising a control and processing device which is connected to the stator coil and which is designed to activate the stator coil in a manner such that a predefined voltage is induced in the rotor coil.

9. The blood pump of claim 4, wherein the pump comprises a sound source for an energetic coupling to the piezoelectric rotor transducer, or a light source for an energetic coupling to the photodiode.

10. The blood pump of claim 1 further comprising a communication unit for wireless transmission of sensor signals of the sensor, wherein the communication unit is arranged on or in the rotor.

11. The blood pump of claim 10 further comprising a rotor coil, wherein the rotor coil is designed as a first communication unit as well as an energy transducer.

12. The blood pump of claim 10 further comprising a coding unit configured to code signals of the sensor and to lead the coded signals further to the communication unit.

13. The blood pump of claim 1, wherein the sensor is an acceleration sensor, a gyroscope, a force sensor, a flow sensor, an oxygen sensor, a $CO_2$ sensor, a proximity sensor, a light sensor, a position sensor, a pressure sensor, a temperature sensor, a magnetic field sensor, a coil, an RFID-sensor, or a pH-sensor.

14. A pump device comprising:
a blood pump comprising:
    a pump casing;
    a rotor which is mounted in the pump casing, the rotor comprising:
        a sensor mounted on the rotor and configured to detect a physiological parameter, a physical parameter, a flow parameter, and/or a movement parameter; and
        an energy transducer configured to supply wireless energy to the sensor or an energy store configured to supply energy to the sensor or wherein the sensor is energy self-sufficient; and
a control and processing unit configured to:
    process and/or evaluate sensor signals from the sensor; and
    activate the blood pump based on the sensor signals.

15. The pump device of claim 14, wherein the sensor is further configured to detect deviations of a rotation of the rotor about a rotation axis.

16. The pump device of claim 14, wherein the control and processing unit is further configured to:
    obtain, based on the sensor signals, information on a condition of the blood pump, information on arising clots on a spiral of the rotor or pump region, and information on a condition of the mounting to the rotor.

17. A method comprising:
operating a blood pump, the blood pump comprising a pump casing and a rotor which is mounted in the pump casing with a sensor, wherein the rotor comprises an energy transducer configured to supply wireless energy to the sensor or comprises an energy store configured to supply energy to the sensor or wherein the sensor is energy self-sufficient; and
detecting a physiological parameter, a physical parameter, a flow parameter, and/or a movement parameter by the sensor mounted on the rotor or disposed in the rotor.

18. The method of claim 17, wherein the physiological parameter, the physical parameter, the flow parameter, and/or the movement parameter are detected during operation of the pump or on a rotation of the rotor.

19. The method of claim 18, further comprising:
detecting, by the sensor, deviations of the rotation of the rotor about a rotation axis.

20. The method of claim 18, wherein the detecting the movement parameter further comprises:
detecting an acceleration of the rotor.

* * * * *